United States Patent
Raupach

(10) Patent No.: US 8,548,216 B2
(45) Date of Patent: Oct. 1, 2013

(54) METHOD FOR NOISE REDUCTION OF CT IMAGES AND IMAGE PROCESSING SYSTEM

(75) Inventor: Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 971 days.

(21) Appl. No.: 12/591,871

(22) Filed: Dec. 3, 2009

(65) Prior Publication Data

US 2010/0166277 A1    Jul. 1, 2010

(30) Foreign Application Priority Data

Dec. 30, 2008    (DE) .......................... 10 2008 063 311

(51) Int. Cl.
    *A61B 6/03*    (2006.01)
(52) U.S. Cl.
    USPC .......................................................... 382/131
(58) Field of Classification Search
    USPC ................... 378/4–5; 382/128–132
    See application file for complete search history.

(56) References Cited

U.S. PATENT DOCUMENTS

| | | | |
|---|---|---|---|
| 4,463,375 A | 7/1984 | Macovski | |
| 4,792,900 A | 12/1988 | Lauro | |
| 6,985,636 B1 | 1/2006 | Semenchenko | |
| 7,650,023 B2 | 1/2010 | Fischer et al. | |
| 2005/0190984 A1 | 9/2005 | Fischer et al. | |
| 2008/0135789 A1 | 6/2008 | Du | |

FOREIGN PATENT DOCUMENTS

DE    102004008979 B4    12/2006

OTHER PUBLICATIONS

Borsdorf et al., Wavelet Based Noise Reduction in CT-Images Using Correlation Analysis, Nov. 21, 2008, IEEE Transactions on Medical Imaging, vol. 27, No. 12, pp. 1685-1703.*
A comparison of noise and dose in conventional and energy selective computed tomography: Alvarez, R.; Seppi, E. In: IEEE Transactions on Nuclear Science, vol. 26, No. 2, pp. 2853-2856; Magazine; 1979.

* cited by examiner

*Primary Examiner* — Toan Ton
*Assistant Examiner* — John Corbett
(74) *Attorney, Agent, or Firm* — Harness, Dickey & Pierce, P.L.C.

(57) ABSTRACT

A method is disclosed for noise reduction of CT image data and an image processing system is disclosed. An object under examination is scanned and at least two CT image datasets are created, each being undertaken on the basis of a different x-ray generation process. Subsequently, the image datasets are split up into at least two split-up image datasets, with a lowest local frequency band and at least one high local frequency band. In at least one embodiment, this is followed by the determination of the noise in at least one of the image datasets for each x-ray spectrum and calculation of at least one new image dataset using an unchanged split-up image dataset in each case with the lowest frequency band and an image dataset created from a noise-minimized weighted combination of split-up image datasets, which originate from the scans with different x-ray energy spectrums.

20 Claims, 3 Drawing Sheets

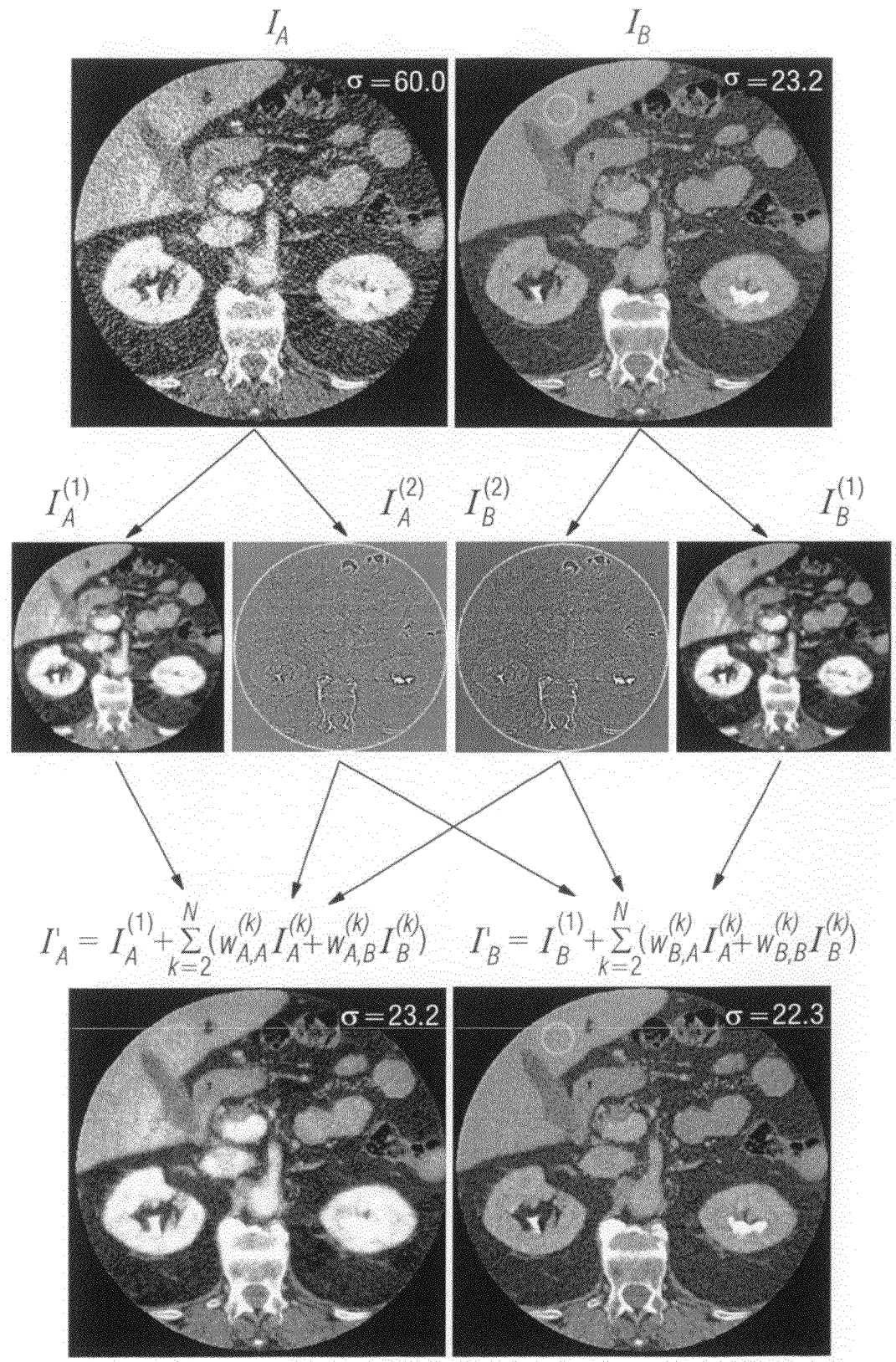

METHOD FOR NOISE REDUCTION OF CT IMAGES AND IMAGE PROCESSING SYSTEM

PRIORITY STATEMENT

The present application hereby claims priority under 35 U.S.C. §119 on German patent application number DE 10 2008 063 311.9 filed Dec. 30, 2008, the entire contents of which are hereby incorporated herein by reference.

FIELD

At least one embodiment of the invention generally relates to a method for noise reduction of CT images from what is known as a dual-energy CT scan. In at least one embodiment it relates to a method in which an object in a computed tomography system, which can be operated with two different x-ray energy spectrums, is scanned with these different x-ray energy spectrums and a computed tomographic sectional image or a volume dataset is created for each spectrum from the same spatial situation. In addition at least one embodiment of the invention also generally relates to an image processing system for executing the method.

BACKGROUND

With dual-energy scans executed with such dual-energy CT systems the primary objective is to extract the multi-spectrum information which is contained in the image data from the different x-ray energy spectrums. This requires low-noise input images from the two spectrums, preferably this image data should exhibit a similar noise level.

As regards the CT system itself, dual-energy imaging is primarily limited by the maximum quanta flow in the low-energy spectrum. An increase in the flow in the high-energy spectrum to reduce the overall noise is actually possible, but does not bring any significant gain in the evaluation of the dual-energy CT images and, even with a noise-weighted sum image, leads to a worse contrast-to-noise ratio than would be theoretically possible for evenly-distributed noise.

It is known from the prior art that for processing this CT image data, edge-retaining noise reduction methods can be applied to the image data recorded with different spectrums. In relation to this method the reader is referred to DE 10 2004 008 979 by way of example, the entire contents of which are hereby incorporated herein by reference. The disadvantage of the method described therein is that the entire information contained in the data is not able to be used, but that each spectrum is regarded as a self-contained scan and is dealt with in relation to its noise reduction.

SUMMARY

In at least one embodiment of the invention, at least one of a method and an image processing system allow a number of items of CT image data of an object to be used based on spectrally different x-ray scans, in order to reduce the noise present in CT image data across the spectrums.

The inventor has recognized, in at least one embodiment, that in dual-energy CT image data of two x-ray energy spectrums, the spectrally-related differences are essentially to be found in lower frequency bands and the high-frequency information is strongly correlated however. At the same time a majority of the noise power is to be found at high frequencies. Accordingly the image data can be divided up into individual frequency bands—in relation to its local frequencies, the image components of the high frequency bands can be combined in a noise-optimized and cross-spectrum manner, whereas low-frequency image components remain largely unaffected. Subsequently the unchanged low-frequency components can be recombined with the image components combined in a noise-optimized and cross-spectrum manner back into a complete image. This allows noise to be greatly reduced and the spectrally-related image information to be largely retained. In particular the method is especially effective when the noise of the image data recorded with different x-ray spectrums differs greatly. In practice the noise of the image data from the low-energy spectrum is mostly significantly higher than the noise of the image data from the higher-energy spectrum.

This basic principle illustrated above can be usefully applied by using the following method. For simplification only one axial layer is considered, but the method described can also be easily transferred by the person skilled in the art to corresponding volume image data from dual-energy scans.

Two dual-energy CT images $I_A$ and $I_B$ of spectrums A and B are broken down into two or more frequency bands $I_A^{(k)}$ or $I_B^{(k)}$ respectively with filters $F_k$ (k=1, ..., N; N≥2), i.e.:

$$I_A^{(k)} = F_k * I_A \text{ or } I_B^{(k)} = F_k * I_B \text{ applying.} \qquad (1)$$

The filters should fulfill the condition $$\sum_{k=1}^{N} F_k \equiv 1,$$

so that $$\sum_{k=1}^{N} I_A^{(k)} = I_A$$

and $$\sum_{k=1}^{N} I_B^{(k)} = I_B$$

apply. Without any restriction k=1 would now correspond to the frequency band with the lowest local frequencies.

For all k>1 local weights are now defined $w_{A,A}^{(k)}$, $w_{A,B}^{(k)}$, $w_{B,A}^{(k)}$, $w_{B,B}^{(k)}$ such that $w_{A,A}^{(k)} + w_{A,B}^{(k)} = 1$ and $w_{B,A}^{(k)} + w_{B,B}^{(k)} = 1$ apply. The resulting images can be defined by $$I'_A = I_A^{(1)} + \sum_{k=2}^{N} \left( w_{A,A}^{(k)} I_A^{(k)} + w_{A,B}^{(k)} I_B^{(k)} \right), \qquad (2a)$$

and $$I'_B = I_B^{(1)} + \sum_{k=2}^{N} \left( w_{B,A}^{(k)} I_A^{(k)} + w_{B,B}^{(k)} I_B^{(k)} \right). \qquad (2b)$$

Preferably the weights are selected in accordance with the noise variance distribution in the band k, i.e. the following applies:

$$w_{A,A}^{(k)} = w_{B,A}^{(k)} = \frac{\left(\sigma_B^{(k)}\right)^2}{\left(\left(\sigma_A^{(k)}\right)^2 + \left(\sigma_B^{(k)}\right)^2\right)}, \quad (3a)$$

and $$w_{A,B}^{(k)} = w_{B,B}^{(k)} = \frac{\left(\sigma_A^{(k)}\right)^2}{\left(\left(\sigma_A^{(k)}\right)^2 + \left(\sigma_B^{(k)}\right)^2\right)}, \quad (3b)$$

if $(\sigma_A^{(k)})^2$ or $(\sigma_B^{(k)})^2$ respectively represent the noise variances of the image components $I_A^{(k)}$ or $I_B^{(k)}$ respectively.

The result images $I'_A$ or $I'_B$ are now in construction terms a local-frequency-dependent mixture of the two input images. Since these exhibit different contrasts for dual-energy CT because of the different x-ray energy spectrums, a local-frequency-dependent contrast is eventually available. In such cases a noise reduction occurs through weighted averaging.

If the frequency bands are selected so that practically the entire noise power is contained in the bands with k>1 then the result images $I'_A$ and $I'_B$ exhibit roughly the same noise for the weighting proposed above. With a very unequal distribution of the noise in the input images a markedly greater noise reduction is produced in the image with the higher noise.

Basically a number of implementation options present themselves. The band filter can be implemented as folding in the local space or as a sequence of a Fourier transformation, a multiplication by filter coefficients in the frequency space and concluding inverse Fourier transformation. In the latter case the weighting is advantageously undertaken in the frequency space so that only one Fourier transformation as well as an inverse Fourier transformation are necessary for the images in each case. Accordingly a wavelet transformation can also be used for subdivision into frequency bands.

As an alternative to processing of the complete reconstructed CT images the filtering can also be carried out on the folding cores already used in the reconstruction of the CT images $\hat{F}_k$ by multiplication of additional factors. This saves any application of Fourier transformations for splitting up the band, but does require the kth number of image reconstructions in relation to the image-based method.

Accordingly the inventor proposes, in at least one embodiment, a method for noise reduction of CT image data which features the following method steps:

Scanning of an object under examination,

Creation of a least two CT image datasets each on the basis of a different x-ray energy spectrum, breaking the image datasets down into at least two split image datasets respectively with a lowest local frequency band (k=1) and at least one high local frequency band (with k=2 . . . N), Determining the noise in at least one of the image datasets per x-ray energy spectrum, Calculation of a least one new image dataset in each case using and unchanged split image dataset with the lowest local frequency band and an image dataset created from a noise-minimized weighted combination of split image datasets which originate from the scans with different x-ray energy spectrums.

Thus with this method the image datasets are broken down into different frequency bands, with advantageously the frequency band being able to be selected such that in one or more higher local frequency bands the noise of the image data is essentially present whereas in at least one low-frequency band image data should be present which is characteristic for the image reproduction by the x-ray energy spectrum used in each case. This provides the option of creating image mixtures with across spectrums in the upper frequency bands which are noise-optimized, i.e. subsequently exhibit minimal noise, and for combining these noise-optimized high-frequency image components with the low-frequency image components of the respective spectrum so that overall for all x-ray energy spectrums present, noise-reduced new image datasets are produced which in addition are strongly uniform in relation to the noise component still present within them. With such image data the multi-spectral information can be used in a more optimum fashion for example within the framework of a multi-material component splitting.

The creation of a number of CT image datasets based on different x-ray energy spectrums can on the one hand be carried out by the original scanning of an object with different x-ray energy spectrums. However the option also exists on the basis of a scanning with a single x-ray energy spectrum and subsequent measurement of the absorption with an energy-selective detector, of creating dual-energy CT images, with only a part of the measured energy spectrum being used per dual-energy CT image.

In relation to the splitting up of the image datasets into different local frequency bands it is proposed on the one hand to carry out this splitting up by filtering with different local frequency filters, in which case it is additionally advantageous to use local frequency filters which are normalized to 1 in their sum.

Alternately there is also the option of carrying out the splitting up of the image datasets by a wavelet transformation, with the local frequency bands being defined by the level of the wavelet transformation.

Finally the splitting up of the image datasets can alternately also be carried out by Fourier transformation, with the local frequency bands being defined by the Fourier coefficients assigned to a local frequency.

In relation to the splitting up of the image datasets described above by different methods, such as filtering, wavelet transformation and Fourier transformation, the reader is referred by way of example to the patent application with file reference DE 10 2007 061 935.0, in which case the above-mentioned splitting methods are basically known to the person skilled in the art. The entire contents of DE 10 2007 061 935.0 are hereby incorporated herein by reference.

For example the noise in the present method can be determined in each case in the respective raw image datasets. However the option also exists of determining the noise in a least one split-up image dataset, preferably in an image dataset of a higher local frequency.

Furthermore the noise can be determined both over the entire image dataset or alternately area-by-area in the image dataset, with the weights determined in accordance with the noise also being determined area-by-area.

If the noise is determined area-by-area, there is the option of establishing the noise by pixel-by-pixel over an adjacent image area to be determined in the CT image dataset and calculating the weights pixel-by-pixel accordingly.

As is shown by way of example in the typical application described below, it is advantageous if in the splitting up of the image datasets precisely one high and precisely one low frequency band is selected, with it being especially useful here if it is ensured that the frequency bands are selected such that the noise of the image is primarily reflected in the high frequency band.

In this context it is pointed out that naturally in the some of the split up part images all frequencies contained in the image should likewise be covered so that no individual frequencies are lost or splitting up of the image data and subsequent merging.

It is also advantageous for the new image datasets which without further image processing correspond to the final image datasets, to be calculated in accordance with the following formulae.

$$I'_A = I_A^{(1)} + \sum_{k=2}^{N} \left( w_{A,A}^{(k)} I_A^{(k)} + w_{A,B}^{(k)} I_B^{(k)} \right)$$

and $$I'_B = I_B^{(1)} + \sum_{k=2}^{N} \left( w_{B,A}^{(k)} I_A^{(k)} + w_{B,B}^{(k)} I_B^{(k)} \right),$$

with $w_{A,A}^{(k)}$, $w_{A,B}^{(k)}$, $w_{B,A}^{(k)}$, $w_{B,B}^{(k)}$ representing the mixture weights.

In such cases the mixture weights $w_{A,A}^{(k)}$, $w_{A,B}^{(k)}$, $w_{B,A}^{(k)}$, $w_{B,B}^{(k)}$ can be determined in accordance with the following formulae:

$$w_{A,A}^{(k)} = w_{B,A}^{(k)} = \frac{\left(\sigma_B^{(k)}\right)^2}{\left(\left(\sigma_A^{(k)}\right)^2 + \left(\sigma_B^{(k)}\right)^2\right)}$$

and $$w_{A,B}^{(k)} = w_{B,B}^{(k)} = \frac{\left(\sigma_B^{(k)}\right)^2}{\left(\left(\sigma_A^{(k)}\right)^2 + \left(\sigma_B^{(k)}\right)^2\right)},$$

with the noise in the image datasets of the spectrum A or B respectively being identified by $\sigma_A$ and $\sigma_B$, the indices k specifying the frequency band and $w_{X,Y}^{(k)}$ representing the weight of the contribution of image $I_Y^{(k)}$ to image $I'_X$.

As well as the method described above in its different embodiments, the framework of at least one embodiment of the invention also includes an image processing system with a computer which features a program memory in which computer programs are stored which execute at least one embodiment of the method described above during operation. It is pointed out in this case that such an image processing system can naturally also be part of a computed tomography system and if necessary is also integrated into the control and processing unit of such a computed tomography system.

BRIEF DESCRIPTION OF THE DRAWINGS

The invention is explained below with reference to an example embodiment in greater detail with the aid of the figures, with only the features necessary for understanding the invention being shown in figures. In this case the following reference symbols and variables are essentially used: 1: Dual-energy CT system; 2: First x-ray tubes; 3: First detector; 4: Second x-ray tubes (optional); 5: Second detector (optional); 6: Gantry housing; 7: Patient; 8: Movable patient couch; 9: System axis; 10: Control and processing system; $F_1$: Highpass filter; $F_2$: Lowpass filter; $\hat{F}_k$: Filter function for kth frequency band; f: Local frequency; $f^{(k)}$: kth frequency band; $I_A$: Dual-energy CT image of the first spectrum A; $I_B$: Dual-energy CT image of the second spectrum B; $I_X^{(k)}$: Split-up image of the frequency band k from the spectrum X; $I'_A$: New image of the spectrum A; $I'_B$: New image of the spectrum B; $w_{X,Y}^{(k)}$: Weight of the proportion of the split-up image $I_Y^{(k)}$ to image $I'_X$; $Prg_1$ through $Prg_n$: Computer programs.

The individual figures show:

FIG. 4: diagrams of two dual-energy CT cross-sectional images with frequency band splitting and subsequent recombination of the frequency-selectively split image datasets into two new image datasets with lower noise.

DETAILED DESCRIPTION OF THE EXAMPLE EMBODIMENTS

Figure 1:
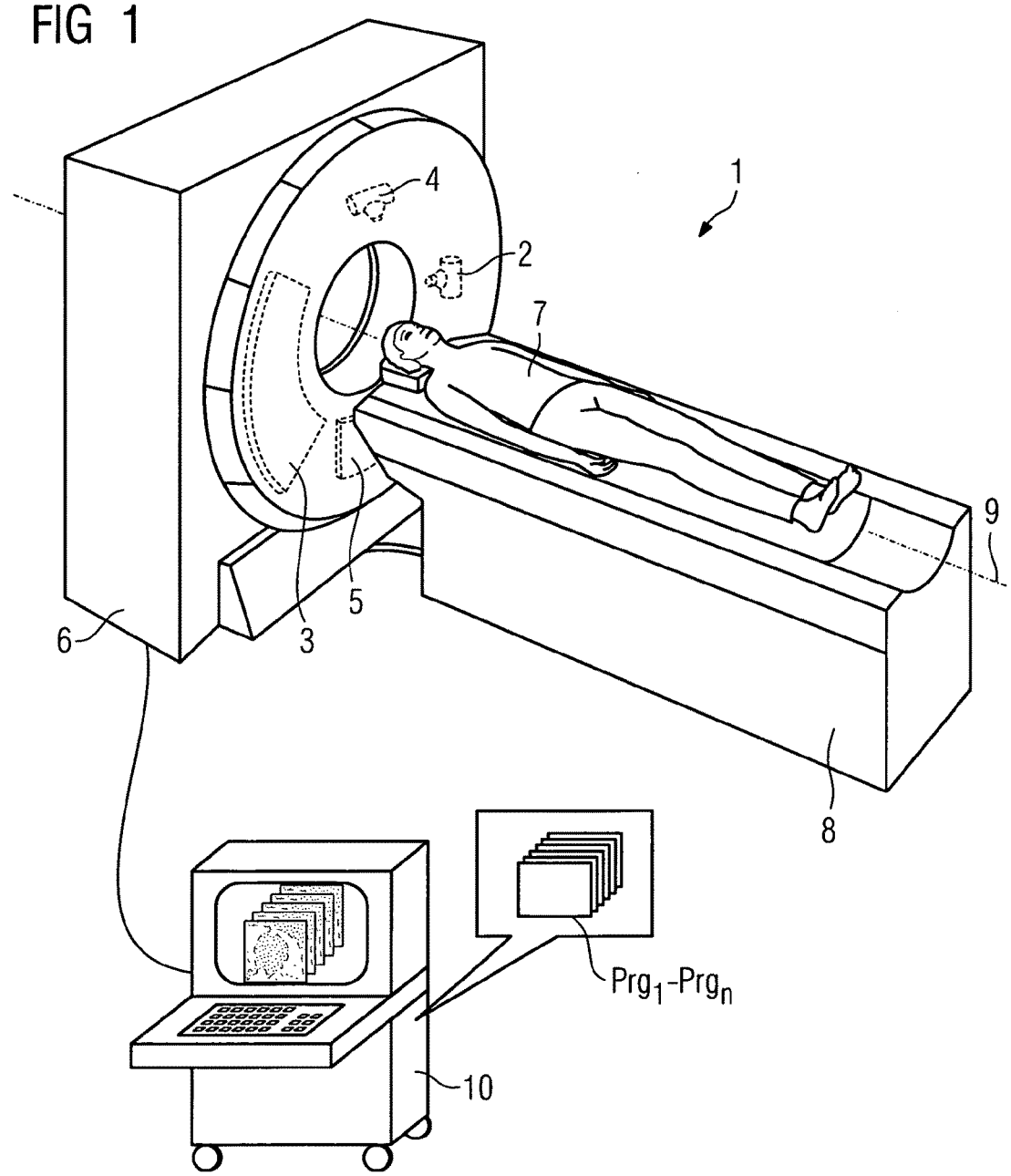
FIG. 1: a dual-energy CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a dual-energy CT system 1 for carrying out an embodiment of the inventive method, with a gantry housing 6 on which two radiator/detector systems are arranged, with a first x-ray tube 2 and a detector 3 lying opposite it, furthermore a second x-ray tube 4 and a detector 5 lying opposite it, with both radiator/detector systems able to be driven with different x-ray energies and simultaneously an object under examination, especially a patient, here 7, able to be scanned with different x-ray energy spectrums. Such a patient 7 is moved during the scanning process continuously or sequentially with the aid of a movable patient cow shoe 8 along a system axis 9 through the measurement field of the CT system, so that the scanning of the patient 7 can be undertaken overall or in specific areas. The CT system 1 can be controlled by the control and processing system 10 also shown schematically in the figure, which contains a program memory in which computer programs $Prg_1$ through $Prg_n$ are stored, which will be executed during operation and which can both control the operation of the CT system and also carry out image processing, where necessary including an embodiment of the inventive method.

Figure 2:
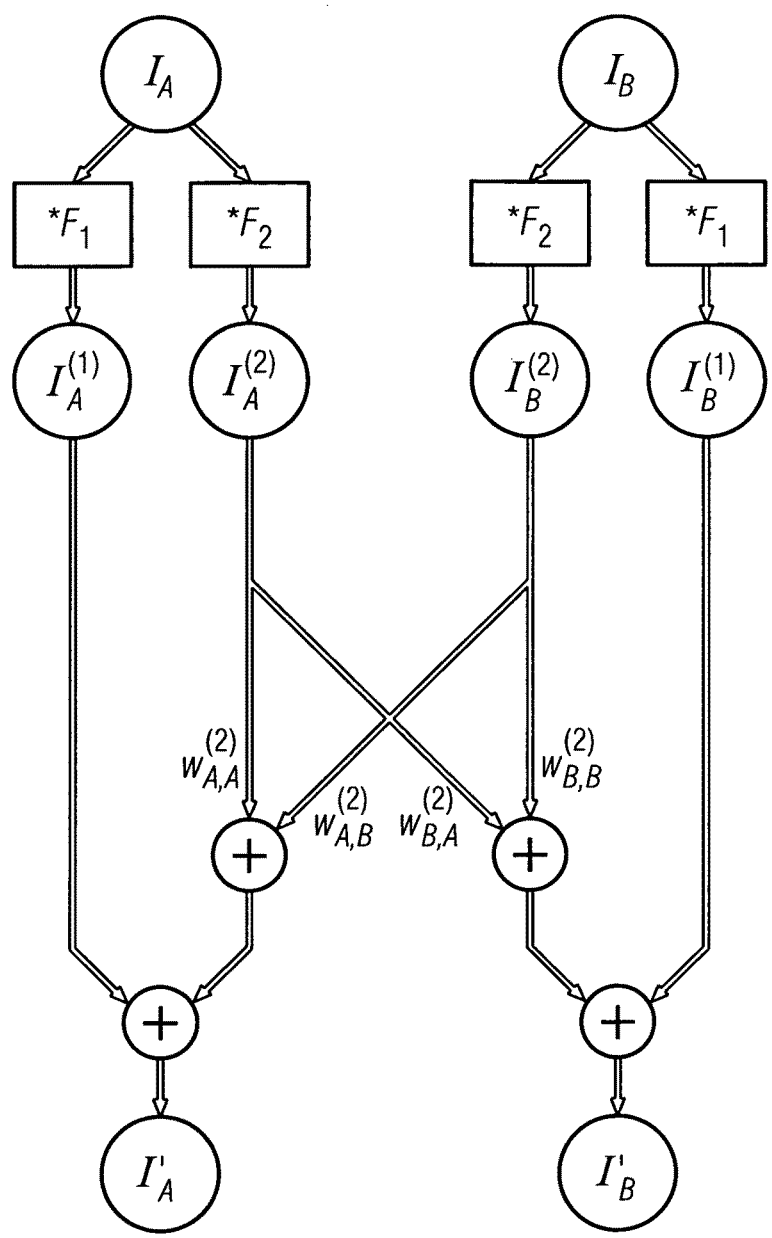
FIG. 2: a schematic diagram of an embodiment of the inventive method with band splitting by filtering and application to a dual-energy CT image dataset.

An embodiment of the inventive method is shown by way of example for the calculation of two sectional images $I_A$ and $I_B$ of two spectrums A and B in FIG. 2. These sectional images $I_A$ and $I_B$ will be divided up with the aid of the filters $F_1$ and $F_2$ into two frequency bands, so that the split-up image datasets $I_A^{(1)}$, $I_A^{(2)}$ are produced in relation to the input image $I_A$ and the two image datasets $I_B^{(1)}$ and $I_B^{(2)}$ split up in accordance with their frequency bands are produced in relation to the input image $I_B$. Inventively the noise in the split-up image datasets $I_A^{(2)}$ and $I_B^{(2)}$ is now determined and their image information is combined noise-optimized in accordance with the weights shown $w_{X,Y}^{(k)}$, with a further combination subsequently being undertaken with the low-frequency split-up image $I_A^{(1)}$ or $I_B^{(1)}$ respectively, so that a new image dataset $I'_A$ and $I'_B$ is produced for each spectrum A and B.

Figure 3:
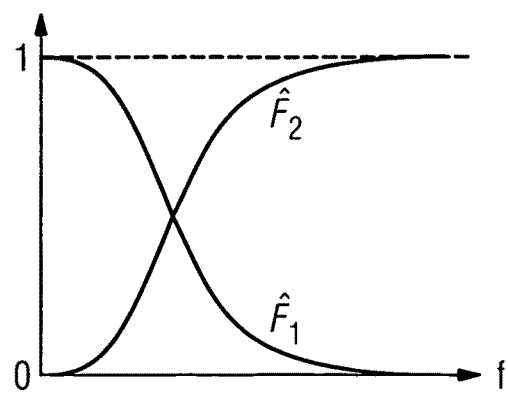
FIG. 3: a frequency curve of two complementary filters for splitting up the image datasets into two frequency bands.

FIG. 3 shows the example of the curve $\hat{F}_1$ and $\hat{F}_2$ of the frequency filters $F_1$ or $F_2$ respectively between 0 and 1 over the local frequency f, as can be used in the method shown in FIG. 2.

To better illustrate the method shown in FIG. 2, the corresponding image data is graphically presented once more in FIG. 4. FIG. 4 shows the input images $I_A$ and $I_B$. $I_A$ corresponds to a CT image with an acceleration voltage of 80 kVp and exhibits a noise in the area delimited by a circle of σ=60. Alongside this to the right is shown a CT image of an identical object with an acceleration voltage of 140 kVp. The noise in the area covered by the circle has the value σ=23.2 here. Inventively these two input images $I_A$ and $I_B$ will be split by filtering into two frequency bands. The result of such splitting is shown in the smaller images presented below. The image $I_A^{(1)}$ shown here corresponds to the image $I_A$ in the lower frequency band, while the image $I_A^{(2)}$ corresponds to the image $I_A$ in the high frequency band. The same is accordingly shown for the image $I_B$ alongside it to the right, with the high frequency band being shown on the left in this image and the low frequency band on the right. Inventively the images split up in this way are combined with each other according to the formulae below, so that new images $I'_A$ and $I'_B$ are produced, with the new image $I'_A$ of the spectrum A now containing a noise of σ=23.2 and the new image $I'_B$ a noise of σ=22.3. As already explained at the start, this means that with this the images have almost approached each other in relation to their noise so that corresponding further calculations, for example for a material splitting, can be carried out significantly more exactly.

It is expressly pointed out that an embodiment of the present method is applicable not only to CT sectional image datasets but also to CT volume datasets and that in addition there is no restriction to image datasets from only two energy areas but image datasets from a number of energy areas can also be handled accordingly.

Furthermore there is also the option of splitting up the image datasets not only into two frequency ranges but into a number of local frequency ranges, will each local frequency range being able to be treated individually in relation to its weighting.

Thus in overall terms a method for noise reduction of CT image data and an image processing system are presented here, with a scanning of one object under examination and creation of a least two CT image datasets $I_A$ and $I_B$, each on the basis of a different x-ray energy spectrum, being undertaken. Subsequently a splitting up of the image datasets $I_A$ and $I_B$ into at least two split-up image datasets $I_A^{(k)}$ and $I_B^{(k)}$ is undertaken in each case, with a lowest local frequency band with the index k=1 and a least one high local frequency band $f^{(k)}$ with the index k=2 through N. This is followed by a determination of the noise $σ_A$ and/or $σ_B$ in at least one of the image datasets $I_A$, $I_B$, $I_A^{(k)}$, $I_B^{(k)}$ per x-ray energy spectrum and calculation of at least one new image dataset $I'_A$ and/or $I'_B$, each using an unchanged split-up image dataset $I_A^{(1)}$, $I_B^{(1)}$ with the lowest local frequency band $f^{(1)}$ and a further image dataset, created from a noise-minimized weighted combination of split-up image datasets, which originate from the scans with different x-ray energy spectrums.

It goes without saying that the features of the invention specified here are able to be used not only in the respective specified combination but also in other combinations or on their own, without departing from the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for noise reduction of CT image data, comprising:
    scanning an object under examination;
    creating at least two CT image datasets, each dataset created on the basis of a different x-ray energy spectrum;
    splitting the at least two CT image datasets into at least two split-up image datasets respectively, with a lowest local frequency band and at least one high local frequency band;
    determining noise in the at least one of at least two CT image datasets for each x-ray energy spectrum;
    calculating at least one new image dataset using an unchanged split-up one of the two CT image datasets with the lowest local frequency band and one of the at least two CT image datasets created from a noise-minimized weighted combination of split-up image datasets which originate from the scans with different x-ray energy spectrums.

2. The method as claimed in claim 1, wherein the scanning is executed with different x-ray energy spectrums.

3. The method as claimed in claim 2, wherein at least one energy-selective detector is used and for image creation, only one part of the measured energy spectrum is evaluated.

4. The method as claimed in claim 1, wherein at least one energy-selective detector is used and for image creation, only one part of the measured energy spectrum is evaluated.

5. The method as claimed in claim 1, wherein the splitting up of the image datasets, is executed by filtering with different local frequency filters.

6. The method as claimed in claim 5, wherein the sum of the local frequency filters used is normalized to 1.

7. The method as claimed in claim 1, wherein the splitting up of the image datasets, is executed by a wavelet transformation and the local frequency bands are determined by the level of the wavelet transformation.

8. The method as claimed in claim 1, wherein the splitting up of the image datasets is executed by Fourier transformation and the local frequency bands are determined by the Fourier coefficients assigned to a local frequency.

9. The method as claimed in claim 1, wherein the noise is determined in each respective raw image dataset.

10. The method as claimed in claim 9, wherein the noise is determined, in each case, over the entire image dataset.

11. The method as claimed in claim 9, wherein the noise is determined area-by area in the image dataset and weights are determined by area for the combination.

12. The method as claimed in claim 9, wherein the noise is calculated pixel-by-pixel from an adjacent image area in the CT image dataset and the weights are calculated pixel-by-pixel.

13. The method as claimed in claim 1, wherein the noise is determined, in each case, by at least one split-up image dataset.

14. The method as claimed in claim 13, wherein the noise is determined, in each case, over the entire image dataset.

15. The method as claimed in claim 13, wherein the noise is determined area-by area in the image dataset and weights are determined by area for the combination.

16. The method as claimed in claim 1, wherein the splitting up of the image datasets into precisely one high and precisely one low frequency band takes place.

17. The method as claimed in one of the previous claims 1 to 16, characterized in that the new image datasets are calculated in accordance with the following formulae:

$$I'_A = I_A^{(1)} + \sum_{k=2}^{N} \left( w_{A,A}^{(k)} I_A^{(k)} + w_{A,B}^{(k)} I_B^{(k)} \right)$$

and $$I'_B = I_B^{(1)} + \sum_{k=2}^{N} \left( w_{B,A}^{(k)} I_A^{(k)} + w_{B,B}^{(k)} I_B^{(k)} \right),$$

with $w_{A,A}^{(k)}$, $w_{A,B}^{(k)}$, $w_{B,A}^{(k)}$, $w_{B,B}^{(k)}$ representing the mixture weights.

18. The method as claimed in the previous claim 17, characterized in that the mixture weights $w_{A,A}^{(k)}$, $w_{A,B}^{(k)}$, $w_{B,A}^{(k)}$, $w_{B,B}^{(k)}$ are determined in accordance with the following formulae $$w_{A,A}^{(k)} = w_{B,A}^{(k)} = \frac{\left(\sigma_B^{(k)}\right)^2}{\left(\left(\sigma_A^{(k)}\right)^2 + \left(\sigma_B^{(k)}\right)^2\right)}$$

and $$w_{A,B}^{(k)} = w_{B,B}^{(k)} = \frac{\left(\sigma_A^{(k)}\right)^2}{\left(\left(\sigma_A^{(k)}\right)^2 + \left(\sigma_B^{(k)}\right)^2\right)}$$

with the noise being designated $\sigma_A$ and $\sigma_s$, the indices k specifying the frequency band and $w_{X,Y}^{(k)}$ representing the weight of the contribution of image $I_Y^{(k)}$ image to $I'_X$.

19. An image processing system comprising:

a computer; and a memory for storing program code, the program code being provided in the memory to execute, during operation, the method claimed in claim 1.

20. A non-transitory computer readable medium including program segments for, when executed on a computer device, causing the computer device to implement the method of claim 1.

* * * * *